United States Patent [19]
Fisher et al.

[11] Patent Number: 5,278,776
[45] Date of Patent: Jan. 11, 1994

[54] SYSTEM AND METHOD FOR THE MEASUREMENT OF MECHANICAL PROPERTIES OF ELASTIC MATERIALS

[76] Inventors: Jack Fisher, 5884 Fredricksburg Dr., Nashville, Tenn. 37215; G. Patrick Maxwell, 4416 Gerald Pl., Nashville, Tenn. 37205; Larry Perry, 3333 Country Ridge Dr., Antioch, Tenn. 37013

[21] Appl. No.: 64,334

[22] Filed: May 19, 1993

Related U.S. Application Data

[63] Continuation of Ser. No. 703,398, May 21, 1991, abandoned.

[51] Int. Cl.$^5$ .................. G06F 15/00; A61B 5/103
[52] U.S. Cl. ...................... 364/508; 364/413.13; 128/774; 73/760; 73/788
[58] Field of Search ............... 364/413.13, 508, 550, 364/551.01, 558, 579; 73/18, 37, 37.5, 760, 788, 789, 800, 834, 835, 837, 838, 840; 128/660.02, 749, 752, 774

[56] References Cited

U.S. PATENT DOCUMENTS

| | | | |
|---|---|---|---|
| 4,569,358 | 2/1986 | Gormley | 128/774 |
| 4,693,255 | 9/1987 | Beall | 128/654 |
| 4,922,909 | 5/1990 | Little et al. | 128/774 X |
| 4,967,602 | 11/1990 | Norton | 73/840 |
| 4,976,272 | 12/1990 | Bazin et al. | 128/774 |
| 5,054,502 | 10/1991 | Courage | 128/774 |

FOREIGN PATENT DOCUMENTS 0255809 2/1988 European Pat. Off. .
2068567 8/1981 United Kingdom .

OTHER PUBLICATIONS

Cook et al, "Experimental Method for Determining the 2-Dimensional Mechanical Properties of Living Human Skin", Medical and Biological Engineering & Computing, Jul. 1977.
Mohan et al., "Failure Properties of Passive Human Aortic Tissue II-Biaxial Tension Tests".
Charles et al., "An Improved Method of Wound Disruption and Measurement".
Cahill et al., "In Vivo Test System for Characterization of Skin Wound Healing", 154, 1987-Paper #87-0105.

*Primary Examiner*—Kevin J. Teska
*Assistant Examiner*—Edward J. Pipala
*Attorney, Agent, or Firm*—Renner, Otto, Boisselle & Sklar

[57] ABSTRACT

A system and method for measuring the biomechanical properties of a healing wound in a specimen which utilize a chamber for applying an increasingly negative pressure over time to an area of tissue containing the wound, markings on the area for facilitating measurement of expansion of the area, a pressure measurement device for measuring the pressure in the chamber as a function of time, one or more cameras for obtaining multiple views of the area over time, a digitizer for generating a digital representation of each of the views, and a processor for determining a strain value from each digital representation and for correlating each strain value with a pressure measurement corresponding to the same point in time to provide a stress-strain relationship.

18 Claims, 4 Drawing Sheets

SYSTEM AND METHOD FOR THE MEASUREMENT OF MECHANICAL PROPERTIES OF ELASTIC MATERIALS

This is a continuation of copending application Ser. No. 07/703,398 filed on May 21, 1991 now abandoned.

FIELD OF THE INVENTION

The present invention relates generally to a method and apparatus for measuring mechanical properties of a material; and, more specifically, to a method and apparatus for measuring certain biomechanical properties of a wound healing in tissue.

BACKGROUND OF THE INVENTION

The medical industry has desired to accurately measure the strength of a healing wound in tissue for a variety of reasons. With recent new interest in cytokines, growth factors, and fetal regeneration, biomechanical studies of wound healing and tissue strength are becoming increasingly more important.

The test specimens for such wound healing tests are laboratory animals, most typically rats. Conventionally, a cut or incision is made on the animal, such as on the abdominal area, and the wound is permitted to heal for a certain time, typically a number of days. The pelt or skin area around the wound is then carefully excised and the excised area mounted in a vise-like device. This device, called an Instron tensiometer, then stretches the pelt transversely to the wound direction and the breaking strength of the wound is measured. Unfortunately, this method introduces a number of factors tending to degrade the accuracy and usefulness of the test as the wound must be excised and measured in vitro or outside of the body. For example, upon excision the pelt begins decomposition effecting its biomechanical properties and the excising and handling of the pelt introduce stresses which may affect the strength and sometimes even rupture relatively new wounds.

Another conventional in vitro method of wound strength testing is performed using an air insufflated positive pressure device. However, this method also requires that the pelt be excised. In this method the excised pelt is mounted between rings often with a thin elastic diaphragm behind it and is subjected to positive pressure until the wound ruptures. Again, since the wound area is excised and manipulated extensively, a great amount of error is introduced into the test.

While these methods have produced generally acceptable rupture strength results for wounds which have healed for several days, the error introduced is unacceptable on fragile and recent wounds and often significantly obscures the results of tests on wounds imparted less than a few days before testing and on fragile fetal wounds. Compounding the disadvantages of these in vitro methods is the fact that it is during the first few days after wounding when the wound is still quite fragile that many of the drugs for which the effects are being tested exhibit their most marked effect on wound healing. Further, since in vitro skin characterization methods require excision of the wound, subcutaneous attachments and fibrin deposits which contribute to wound strength are necessarily disrupted.

It would be desirable to test wounds with an increased accuracy and repeatability, particularly with respect to relatively recent and otherwise fragile wounds such as fetal wounds. It would also be desirable to measure biomechanical properties of skin in vivo, thus more closely measuring actual conditions when the skin is connected to subcutaneous material. It would be further desirable to measure biomechanical skin properties, such as elasticity, etc. without subjecting the specimen to the trauma of excising, thus even permitting limited biomechanical measurements, without rupture, on humans.

SUMMARY OF THE INVENTION

The present invention provides an apparatus for measuring in vivo certain mechanical and biomechanical properties of materials and tissues such as wounded skin. The apparatus is particularly effective for testing the properties of fragile wounds, such as those imparted only a few days before testing and fetal tissue wounds.

In accordance with one aspect of the present invention, a device for measuring the biomechanical properties of a healing wound in a specimen includes a chamber for applying an increasingly negative pressure over time to an area of tissue containing the wound, the area having markings for facilitating measurement of expansion of the area, a pressure measurement device for measuring the pressure in the chamber as a function of time, a camera for obtaining multiple views of the area over time, a digitizer for generating a digital representation of each of the views, and a processor for determining a strain value from each digital representation and for correlating each strain value with a pressure measurement corresponding to the same point in time to provide a stress-strain relationship.

In accordance with another aspect of the invention, a device for measuring the mechanical properties of an elastic material includes a chamber for applying an increasingly negative pressure over time to an area of the material, the area including indicia facilitating measurement of deformation of the area, a pressure measurement instrument for measuring the pressure in the chamber as a function of time, a camera for obtaining a number of views of the area over time, a digitizer for generating a digital representation of each of the views, and a processor for determining an expansion ratio from each digital representation and for correlating each expansion ratio with a pressure measurement corresponding to the same point in time.

In accordance with a further aspect of the invention, a method of measuring the mechanical properties of an elastic material includes the steps of marking the material with indicia facilitating tracking the expansion of the material, applying an increasingly negative pressure over time to an area of the material including the indicia, measuring the pressure applied to the area as a function of time, obtaining a plurality of views of the area over time, generating a digital representation of each of the views, and determining certain mechanical characteristics of the material from the measured pressure and the generated digital representations.

These and other objects, advantages, features and aspects of the present invention will become apparent as the following description proceeds.

To the accomplishments of the foregoing and related ends, the invention, then comprises the features hereinafter fully described in the specification and particularly pointed out in claims, the following description and the annexed drawings setting forth in detail a certain illustrative embodiment of the invention, this being indicative, however, of but one of the various ways in which the principals of the invention may be employed. It will be appreciated that the scope of the invention is to be determined by the claims and the equivalents thereof.

DETAILED DESCRIPTION OF THE INVENTION

Figure 1:
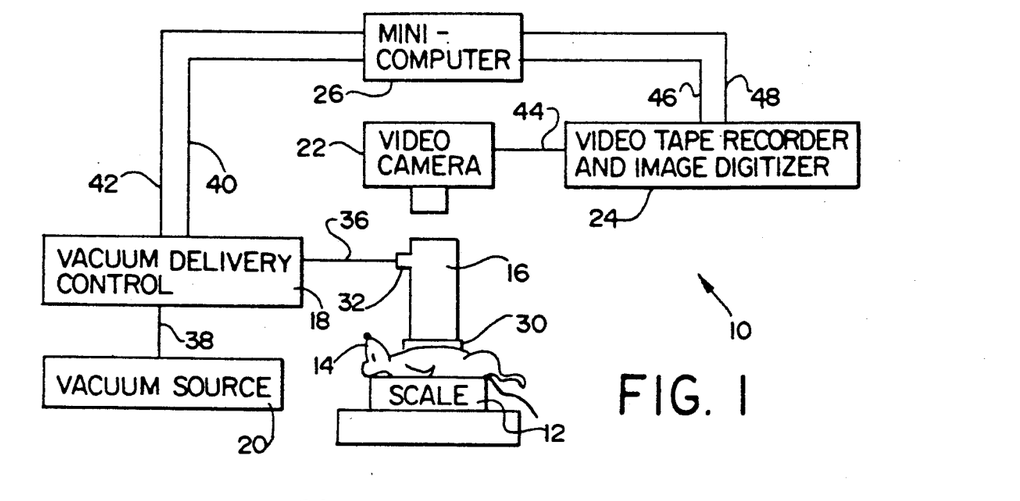
FIG. 1 is a block diagram of a Vacuum Controlled Wound Chamber Device for in vivo testing of biomechanical skin properties in accordance with the present invention.

With reference to the several figures in which like reference numerals depict like items, and initially to FIG. 1, there is shown a block diagram of a Vacuum Controlled Wound Chamber Device (VCWCD) 10 for measuring in vivo certain biomechanical properties of a healing wound. The VCWCD 10 includes a scale 12 upon which a specimen 14 having the wound is placed, a vacuum chamber 16 for the application of a negative pressure to the wound area, a vacuum controller 18, a vacuum source 20, one or more video cameras or charge coupled devices 22 having a view of the wound, a video recorder and image digitizer 24 and a processing system 26.

The specific embodiment of the VCWCD 10 illustrated and described relative to FIG. 1 is one designed to use a laboratory rat as the test specimen having the healing wound which is tested. It will be appreciated, however, that the VCWCD 10 may be modified in a variety of ways to perform tests on other animal specimens or on nonbiological materials, all of such modifications being within the scope of the invention. Further, the operation of the VCWCD 10 will be described below relative to a wound incised in the abdomen of the laboratory rat, it being apparent that the site of the wound is but a specific parameter of the test and that other wound sites may be chosen to evaluate the biomechanical properties of healing wound tissue at other locations of the animal. Additionally, it is noted that the empirical data provided herein for the VCWCD 10, the Instron tensiometer, and the Air Insufflated Positive Pressure Device (AIPPD), was accumulated through tests performed with the respective devices in accordance with the National Research Council's guide for the care and use of laboratory animals.

The scale is preferably an adjustable electronic scale which can be tared to the weight of the test specimen, such as a Sartorius 1000MP9 scale manufactured by Tennessee Scale Works. Positioned directly above the specimen 14 disposed on the scale 12 and in contact with a ring 30 (shown greater detail in FIG. 3) secured to the skin of the specimen is the vacuum chamber 16. The vacuum chamber 16 is of a generally cylindrical shape having an inner diameter for instance of 2.5 cm and is adapted to form a pressure seal with the ring 30. The vacuum chamber 16 is preferably constructed of glass with at least the top portion of the vacuum chamber being transparent to allow a view of the wound to be taken by the video camera 22 which is positioned directly above the vacuum chamber. The vacuum chamber 16 also includes an orifice 32 for communication with the vacuum source 20. Both the vacuum chamber 16 and the video camera 22 are vertically adjustable to accommodate the position of the specimen and to permit the vacuum chamber and camera to be lowered into a position where the chamber is in intimate contact with the ring 30 while exerting minimal pressure on the ring and the wound area.

The pressure in the vacuum chamber 16 is controlled by the vacuum controller 18 which adjusts the rate of communication with the vacuum source 20. The vacuum controller 18 preferably includes a 248-10000 SV control valve, a 250C controller, and a TORR type 122-AA-01000AB pressure transducer, all manufactured by MKS Instruments. The vacuum source 20 is essentially a pump which maintains a very large volume at a very low pressure, the volume being large enough and the pressure being low enough to create a negative pressure in the vacuum chamber 16 sufficient to rupture the wound. Consequently, when the vacuum controller 18 opens communication between the vacuum source 20 and the vacuum chamber 16, the air within the vacuum chamber will be evacuated through the orifice 32 and suitable pressure lines, shown schematically as 36 and 38 in FIG. 1, to the vacuum source at a rate controlled by the vacuum controller.

The action of the vacuum controller 18 is controlled by the processing system 26 through a control signal shown schematically at 40. The vacuum controller 18 provides an analog electrical signal 42 proportional to the negative pressure in the vacuum chamber 16 to the processing system 26 which converts the analog signal to a digital equivalent and stores the digital pressure data as a function of time.

The video camera 22 obtains a video image of the wound area of the specimen through the vacuum chamber 16 and transmits that video image to the video recorder and image digitizer 24 over the line 44. In other embodiments of the invention it may be desirable to employ more than one video camera to obtain different views of the wound area. The video recorder and image digitizer 24 is preferably a Panasonic AG6300/60 Hertz video recorder/playback unit and a Motion Analysis Corporation VP-110 Dynamic Image Processor equipped with a suitable interface to the processing system 26. Upon receiving an appropriate command from the processing system 26 over the line 46 in the form of an audio signal, the video recorder and image digitizer 24 (hereinafter, image digitizer) will begin to record the video signal from the video camera 22 on suitable VHS recording media and to digitize the video signal at a specific rate, such as two frames of digitized image data per second. These frames, which are digitized images of the wound area, are collected and stored until the end of the test. Typically, 150 frames of digital images will adequately represent the test from the time when the initial vacuum is applied to the wound until the wound disrupts. Once all data has been collected for a test, the image digitizer 24 will transfer the digital image frames to the processing system 26 over the line 48.

Upon completion of a test, the processing system 26 will have obtained the pressure data as a function of time from the vacuum controller 18 as well as the digital images of the wound during the test as a function of time from the image digitizer 24. The processing system 26 thus has sufficient data to allow the calculation of certain biomechanical properties, such as stress-strain relationships and modulus of elasticity, for the wound being tested. The processing system 26 also provides sufficient storage to allow the accumulation of data from several tests, thus facilitating the statistical comparison of a series of tests having similar testing parameters, such as wound healing time.

Figure 2:
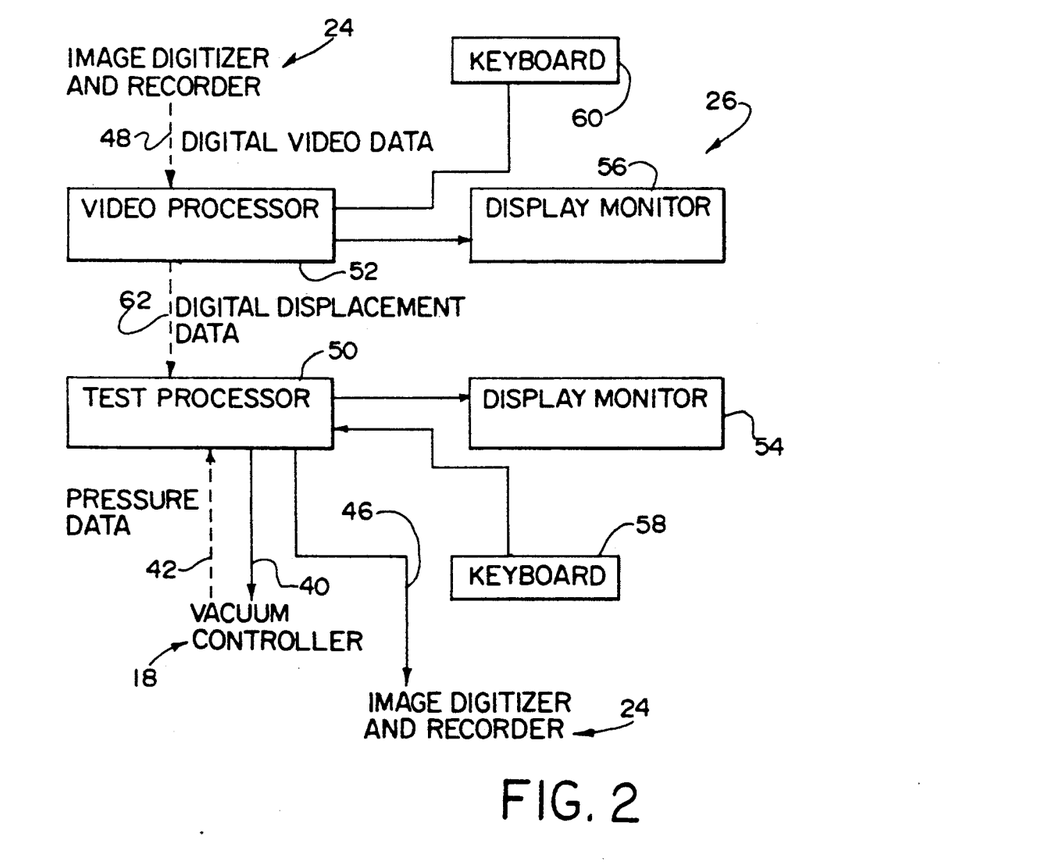
FIG. 2 is a block diagram of the processing system of the Vacuum Controlled Wound Chamber Device.

The processing system 26 is shown in greater detail in FIG. 2. In the figure dashed lines indicate the transfer of data while solid lines indicate control paths. The processing system 26 includes a test processor 50 which performs overall test control and calculates the final biomechanical properties of the test specimen, an image processor 52 which processes the digitized image data, and display monitors 54, 56 and keyboards 58, 60 corresponding to the test processor and the image processor, respectively. The image processor 52 is preferably an IBM TM compatible microcomputer based on an Intel TM 80386 TM microprocessor chip. The image processor 52 preferably includes a dedicated video processing board facilitating the processing of digital image data, such as a video processing board manufactured by Motion Analysis Corporation which is configured for insertion into available slots in IBM TM compatible microcomputers. During operation, the image processor 52 receives digital image frames of the wound area, indicated at 48, collected during a test from the image digitizer 24, processes those frames to determine the location of specific dot indicators (which are applied to the skin as described hereinafter) in the image and correlates the coordinates of the dot indicators with the time from the beginning of the test. The keyboard 60 and display monitor 56 associated with the video processor 52 allow user interaction with the image processor 52, thereby allowing the user to input specific data to the image processor and permitting the user to edit digital displacement data to eliminate extraneous data, such as that data collected before a vacuum was applied in the vacuum chamber and data collected after the wound was disrupted. The correlated, edited data 62 is then made available for transfer to the test processor 50.

The test processor 50 is preferably also an IBM TM compatible microcomputer employing an Intel TM 80386 TM based microprocessor chip. The test processor 50 controls the vacuum controller 18 as well as the image digitizer 24. The test processor 50 further receives pressure data 42 from the vacuum controller 18 which it digitizes and coordinates with time from the beginning of a test. The test processor 50 coordinates the pressure data and digital displacement data of the indicator dots and performs calculations of the biomechanical properties of the wound being tested. The keyboard 58 and display monitor 54 associated with the test processor 50 provide user interaction with the test processor and allow the user to edit the digitized pressure data to permit removal of extraneous data, such as that gathered before a pressure was applied to the wound and that collected after the wound disrupted.

To prepare a specimen rat for the test, the rat is administered phenobarbital anesthesia intraperitoneally. An area of the rat, such as the abdomen, is then shaved and cleaned. Using a template, a guide is drawn for a midline abdominal incision of 2.5 cm, for example, and a full thickness incision is made following the guide. The wound is then closed, such as with surgical staples, and the animal is returned to its cage. The animal is fed ab libitum until the strength of the healing wound is tested.

Figures 3, 4A:
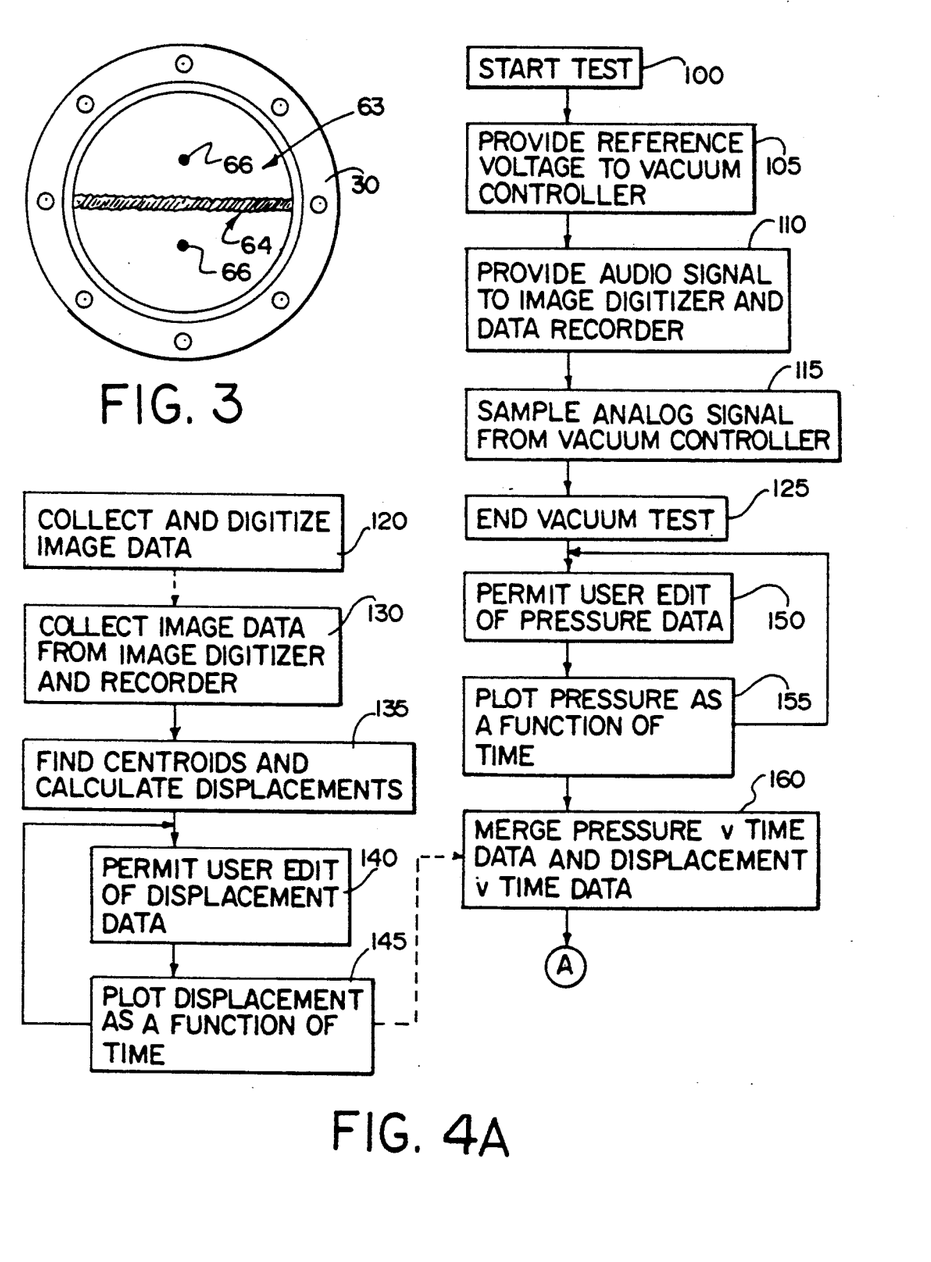
FIG. 3 is an illustration of a wound on the abdominal region of a laboratory rat showing a ring and positional dot markings utilized in the test.
FIGS. 4A and 4B represent a flowchart of the operation of the Vacuum Controlled Wound Chamber Device.

When it is desired to test the strength of the wound, the rat is anesthetized and the circular ring 30 having an inner diameter substantially corresponding to the length of the wound incision, for example 2.5 cm, is secured, such as by gluing with cyanocrylate and/or using surgical staples. Any surgical staples used previously to close the incision are then removed. The effect of the circular ring 30 is to isolate the skin subject to the vacuum to a circular or truncated spherical area of the skin, thus removing the contributions to the stress on the wound by the surrounding skin areas and providing a uniform surface for an airtight seal with the vacuum chamber 16.

FIG. 3 illustrates a view of a ring 30 glued to the abdominal tissue 63 of a laboratory rat 14 and positioned with the wound 64 bisecting the area enclosed by the ring into equal halves. A pair of indicator dots 66 are then inked onto the skin of the rat; one on each side of the wound 64 as shown in FIG. 3, such that a line extending between the dots would intersect the approximate midpoint of the wound 64 perpendicular to the longitudinal extent of the wound. While the embodiment of the test described herein employs a pair of indicator dots 66 to facilitate tracking expansion of the tissue during testing, any number of locating indicia may be employed. Further, the wound area may be marked with a matrix of lines forming discrete areas facilitating calculations of stresses, etc., at multiple locations over the wound area such as by finite element methods or by other known methods.

The rat 14 is then placed abdomen up on the scale 12 and the scale is tared. The vacuum chamber 16 and video camera 22 are then lowered until the lower surface of the vacuum chamber is in intimate contact with the ring 30. The scale 12 is checked to ensure that the vacuum chamber 16 does not exert a force upon the rat 14, as such a force may introduce error into the test results.

Figure 4B:
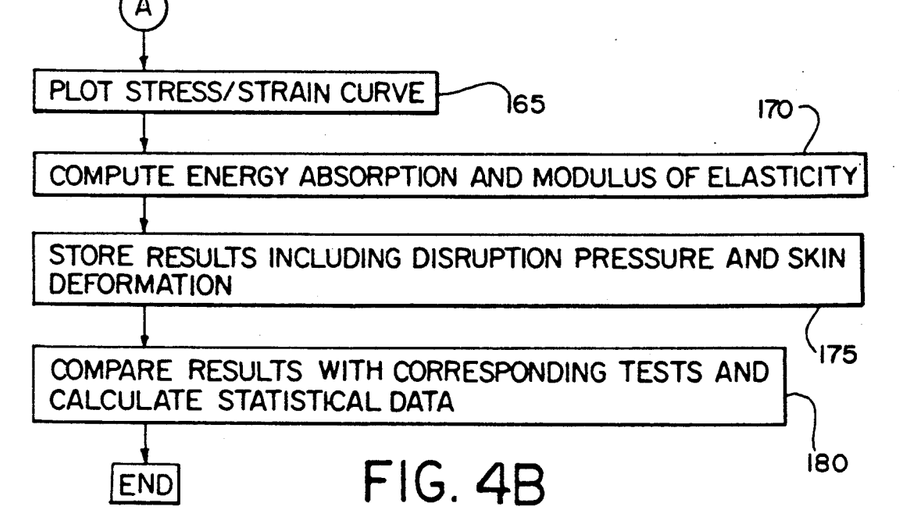

The flowchart of FIGS. 4A and 4B schematically illustrates the operation of the VCWCD 10 during a wound strength test. Note that reference to specific steps in the flowchart of FIGS. 4A and 4B will be denoted in the discussion below by a like reference numeral enclosed in parentheses, that solid lines in the figure represent the functional transfer between specific steps in the flowchart, and that dashed lines denote the flow of data only. The circled "A" at the bottom of the flowchart in FIG. 4A indicates functional transfer to the same symbol at the top of FIG. 4B.

Upon a command to the test processor 50 by an operator, such as though a sequence of appropriate key strokes entered on the keyboard 58, the test is begun (100). The test processor 50 then generates a reference voltage which is sent to the vacuum controller 18 (105) which in response to the signal, begins the controlled reduction of pressure in the vacuum chamber 16. Simultaneously, the test processor 50 sends an audio signal to the image digitizer 24 to command the image digitizer to begin recording image data received from the video camera 22 (110). The test processor 50 then begins sampling an analog electrical signal produced by the vacuum controller 18 which is proportional to the pressure in the vacuum chamber 16 (115). Concurrently, the image digitizer 24 is digitizing and storing digital images taken by the video camera 22 of the wound site at a rate preferably equal to the rate at which the test processor 50 is sampling and digitizing pressure data from the vacuum controller 18, such as two frames per second (120).

The vacuum or negative pressure in the vacuum chamber 16 exerts a force on the skin 63 surrounded by the ring 30. Since skin tissue is an elastic biomaterial, the effected skin will stretch and deflect into the interior of the vacuum chamber 16 in a truncated spherical configuration to tend to relieve the negative pressure in the vacuum chamber. As the skin is continuously stretched by the gradually increasing vacuum, the locator dots 66 inked on the skin 63 on either side of the wound 64 will displace away from the wound and away from each other. While the pressure in the vacuum chamber 16 is continually decreased by the vacuum controller 18 through the communication with the vacuum source 20, the decreasing analog voltage/pressure signal generated by the vacuum controller is sampled by the test processor 50 and the images of the wound area and gradually displacing dots 66 taken by the video camera 22 are stored in a video format and digitized and stored in a digital format by the image processor 24. After a time sufficient for the pressure to have been decreased in the vacuum chamber to the point where the wound has ruptured, the test processor will stop the vacuum test (125).

After completion of the vacuum portion of the test, the image digitizer 24 will transfer the collected image frames to the image processor 52 (130). The image processor 52 will then perform standard processing techniques on the digital images to determine the centroids of the locator dots 66 in each image and to determine the displacement of the centroids from the original distance between the centroids of the dots before a pressure was applied to the wound area (135). Suitable algorithms to provide such image processing functions are known in the art, and commercial software is available which has implemented these functions in executable code appropriate for execution on a variety of processors. Software suitable for use with the preferred image processing board manufactured by Motion Analysis Corporation is also available from Motion Analysis Corporation.

Through the use of the display monitor 56 and keyboard 60 associated with the image processor 52, the operator may then examine the displacement data to identify the point of rupture of the wound, which will be represented in the data as a large, abrupt displacement change, and may edit the data to remove any extraneous data, such as that collected after the wound has ruptured or before the wound was subjected to adequate pressure to begin the test (140). The image processor 52 will then plot the displacements as a function of time on the corresponding display monitor 56 (145) and, aided by the graphical display on the display monitor, the operator is given the option to edit the displacement data again (140). If the operator has chosen to edit the data, the edited displacement data will again be plotted as a function of time (145). This process will continue until the operator is satisfied with the displacement data. The edited displacement data will then be made available to the test processor 50 for correlation with edited pressure data.

The operator is given the opportunity by the test processor 50 to examine and edit the pressure data also (150). Similar to editing the displacement data discussed above, the operator may choose to remove extraneous data from the pressure data, such as the pressure data collected after the wound ruptured. The operator may also identify the pressure when the wound disrupted, which represents the bursting strength of the wound. The test processor 50 will then plot the edited pressure data as a function of time of the display monitor 54 (155) and permit the operator to again edit the pressure data as aided by the graphical representation (150). Once the operator is satisfied with the edited pressure data, the test processor 50 will retrieve the displacement data from the image processor 52, and merge the pressure versus time data with the displacement versus time data to generate pressure (stress) versus displacement (strain) data (160). To the extent that the pressure and displacement data points were collected at identical points in time, they may be simply merged together; in the event that the points are collected at slightly different points in time, they may be merged using standard interpolation techniques.

The pressure is then plotted on the display monitor 54 as a function of displacement to produce a stress versus strain curve for the wound specimen (165). By determining algorithmically or visually, through the aid of the operator, the most linear section of the stress-strain curve, the modulus of elasticity, or the slope of the curve, and the energy absorption, or the total area under the stress-strain curve are calculated (170). The results of the test, including the disruption pressure, the total displacement or deformation at rupture, the modulus of elasticity, and the energy absorption are then stored in a properly identified file for each specimen tested (175). These stored results may at any time be compared to the results of other individual tests or to the results of a series of tests, and statistical data, such as mean values and standard deviations, may be calculated to facilitate comparison of data and accuracy of results (180).

Figure 5:
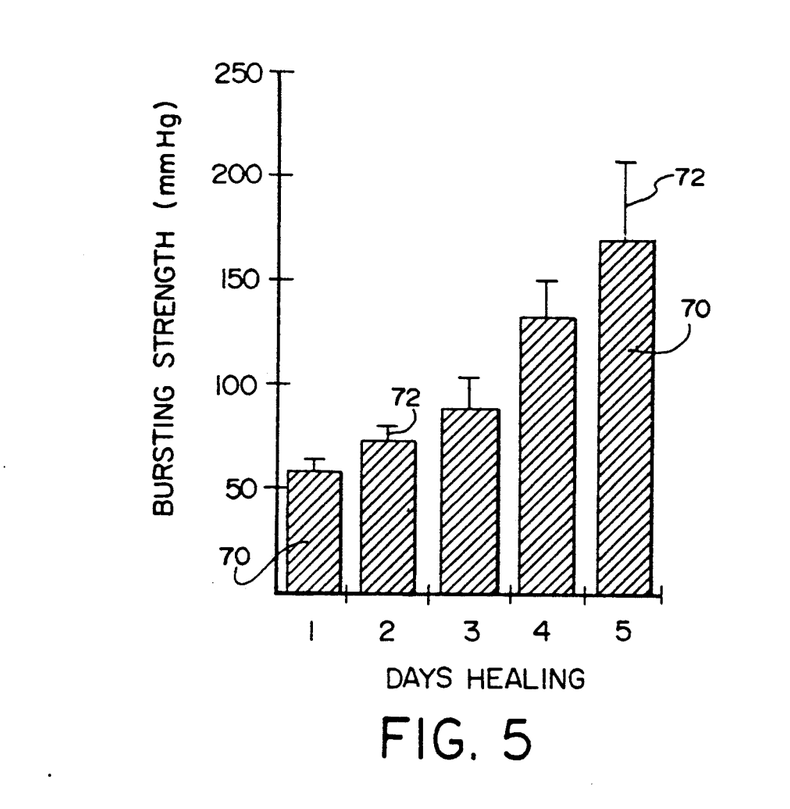
FIG. 5 is a graphical comparison of mean wound disruption strengths and standard deviations for tests performed by the Vacuum Controlled Wound Chamber Device over the first through fifth days following specimen wounding.

To illustrate results obtainable by the VCWCD method, a number of laboratory rats weighing from 250 grams to 300 grams were prepared as described above and divided into five separate groups for measuring wound healing strength each day over a period of five days. The bursting strength results of those tests are illustrated in FIG. 5. In the figure, the hatched columns 70 represent bursting strength in millimeters of mercury while the standard deviation of the tests performed each day is indicated by the length of the bracketed lines 72 extending from the top of the hatched column. As is indicated in the figure, especially in the first few days after wound healing, the standard deviation of the VCWCD test is very small, indicating the accuracy and repeatability of the test.

To illustrate the accuracy of the VCWCD test over the AIPPD and Instron tensiometer tests, 45 laboratory rats weighing from 250 grams to 300 grams were divided into three groups and wound healing strengths studied at 2, 7, and 14 days after wounding using each test method. The laboratory rats were prepared and incised as described above with the exception that only the specimens used in the VCWCD method were marked with indicating dots. In the Instron tensiometer and AIPPD tests the specimens were sacrificed prior to the tests, whereas in the VCWCD test the specimens were sacrificed immediately following completion of the tests.

For the Instron tensiometer test, the abdominal skin of the laboratory specimen containing the wound was excised carefully from the sacrificed animal to avoid introducing distortion in the study area. The tissue was then placed in the clamps of the Instron device and progressive force was applied until the wound disrupted. The breaking strength was calculated based on the grams of force required to break the wound. For tests performed using the AIPPD method, again the abdominal wounds were carefully excised with sharp dissection to avoid distortion of the study area. The excised wounds were then secured on a compressing O ring overlying a 2 cm by 1 cm hole in the top of a cylindrical pressure chamber. The air was insufflated into the chamber until the wounds disrupted and the pressures required to break the wounds were recorded in pounds per square inch using an in-line gauge connected through the insufflation port. Tests performed using the VCWCD method were conducted as described above.

Figure 6:
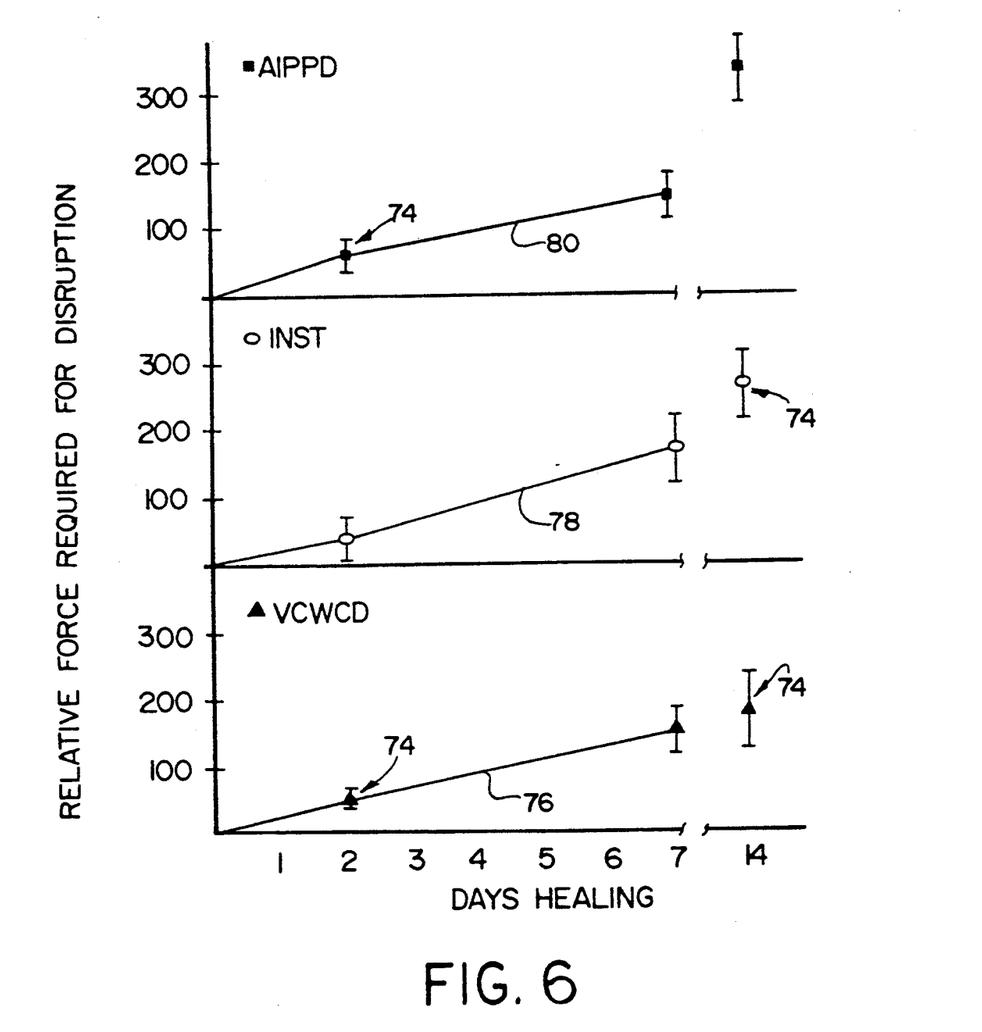
FIG. 6 is a graphical comparison of wound disruption strengths determined by the Vacuum Controlled Wound Chamber Device, the Instron tensiometer and an air insufflated positive pressure device.

The data generated from VCWCD and AIPPD methods were expressed as pounds per square inch while data generated from the Instron tensiometer method was expressed in grams per cross-sectional area. Therefore, to compare the three methods, the data was normalized as a percent of the mean in each data group and as expressed as the mean and standard deviation from the mean. The results of the three methods of wound disruption are presented in FIG. 6 at 2, 7 and 14 days after wounding and in Table 1 below at 2 days after wounding. FIG. 6 is a graph of the mean disruption force as a function of healing time in days. In the graph the bracketed lines 74 indicate the standard deviation at days 2, 7 and 14. The curves 76, 78, 80 illustrate that there is good correlation between all three experimental methods and that the slopes of the curves are similar. There was no statistically significant difference between the slopes of the lines in any of the three methods used.

TABLE 1

A comparison of wound strength measurement using VCWCD, AIPPD and Instron tensiometer techniques at 2 days post wounding. The data was normalized as a percent of mean value.

| OBSERVATIONS | VCWCD[1] | AIPPD[2] | INSTRON[2] |
|---|---|---|---|
| 1 | 1.5 | 2.1 | 3.0 |
| 2 | 1.1 | 2.9 | 0.9 |
| 3 | 1.6 | 1.5 | 1.6 |
| 4 | 1.5 | 3.0 | 1.5 |
| 5 | 1.4 | 2.0 | 4.6 |
| Mean ± Std Dev | 1.42 ± .19 | 2.3 ± .63 | 2.48 ± 1.62 |

Std Dev = Standard Deviation
[1] $p < .05$
[2] Required 8 animals for 5 observations Referring to Table 1 it is seen that the VCWCD test group for day 2 had less standard error in wound measurement than the AIPPD and Instron tensiometer methods, with a standard deviation of only 0.19 for the VCWCD method compared to 0.63 for the AIPPD and 1.62 for Instron tensiometer methods. It is further noted that in the day 2 test for the AIPPD and Instron tensiometer methods, eight animals were required to produce the five observations recorded because the process of excising the wound and mounting it in the respective devices subjected the wounds to sufficient stress to cause disruption in three instances each.

A unique attribute of the VCWCD method is the ability to measure the modulus of elasticity of the wound and the energy absorption from the disruption test. In Table 2 below the mean, standard deviation and the standard deviation expressed as a percent of the mean value are provided for strength, deformation and modulus of elasticity of the VCWCD test specimens at days 2 and 7. Examination of the Table indicates that standard deviation is relatively small for all aspects of the VCWCD test at days 2 and 7. This further indicates that the VCWCD test produces reliable and reproducible data even for immature wounds.

While the specific embodiment of the invention described herein is adapted for the measurement of the biomechanical properties of a wound healing in tissue, the invention has broad applicability in measuring characteristics of many different materials, such as silicone, polyurethane, latex, rubber, and other deformable biomechanical and mechanical materials. The invention may also provide useful information as to the means by which certain elastic materials rupture, such as a material including a small perforation to determine tear strength, for example.

TABLE 2

Typical VCWCD test demonstrating a comparison of Bursting Strength, Skin Deformation and Modulus of Elasticity.

| Variable | n[1] | Mean | Std Dev | % Mean[2] |
|---|---|---|---|---|
| Day 2 | | | | |
| Strength (mm Hg) | 5 | 68.02 | 6.93 | 10% |
| Deformation (mm) | 5 | 4.76 | .51 | 11% |
| Modulus (kPa) | 5 | 36.76 | 6.28 | 17% |
| Day 7 | | | | |
| Strength (mm Hg) | 5 | 246.00 | 32.38 | 13% |
| Deformation (mm) | 5 | 4.06 | 0.62 | 13% |
| Modulus (kPa) | 5 | 214.00 | 29.79 | 14% |

[1] Five specimens were tested.
[2] % Mean = Indicates standard deviation as a percentage of the mean value.

What is claimed is:

1. A device for measuring certain biomechanical properties of a healing wound in a specimen, comprising:
   a) chamber means for applying an increasingly negative pressure over time to an area of tissue containing such wound, marking means on such area for facilitating measurement of expansion of such area;
   b) pressure measurement means for measuring the pressure in such chamber means as a function of time;
   c) camera means for obtaining a sequence of views of such area over time;
   d) digitizer means for generating a digital representation of each of such views; and
   e) processor means for determining a strain value from each such digital representation and for correlating each such strain value with a pressure measurement corresponding to the same point in time to provide a stress-strain relationship.

2. The device of claim 1, wherein such marking means includes a pair of dots, one dot located on each side of the wound.

3. The device of claim 1, including means for calculating the modulus of elasticity of such area from a relatively linear portion of such stress-strain relationship.

4. The device of claim 1, further including means for displaying such pressure measurements and such strain values and for permitting editing of such pressure measurements and such strain values.

5. The device of claim 1, wherein said processor means includes a dedicated image processor.

6. The device of claim 1, wherein said camera means is a video camera.

7. The device of claim 1, wherein said camera means is a charge coupled device.

8. The device of claim 1, further including a display monitor for the display of such stress-strain relationship.

9. A device for measuring certain mechanical properties of an elastic material, comprising:
 a) chamber means for applying an increasingly negative pressure over time to an area of such material, such area including indicia for facilitating measurement of deformation of such area;
 b) pressure measurement means for measuring the pressure in such chamber means as a function of time;
 c) camera means for obtaining a sequence of views of such area over time;
 d) digitizer means for generating a digital representation of each of such views; and
 e) processor means for determining a strain value from each such digital representation and for correlating each such strain value with a pressure measurement corresponding to the same point in time to provide a stress-strain relationship.

10. The device of claim 9, wherein said camera means includes a video camera.

11. The device of claim 9, wherein said camera means includes a charge-coupled device.

12. The device of claim 9, wherein such area is a circular area.

13. A method of measuring the mechanical properties of an elastic material, comprising the steps of:
 a) marking such material with indicia facilitating tracking of any expansion of such material during application of negative pressure to such material;
 b) applying an increasingly negative pressure over time to an area of such material having such indicia to cause such material to expand over time;
 c) measuring the pressure applied to such area as a function of time;
 d) obtaining a sequence of views of such area over time;
 e) generating a digital representation of each of such views; and
 f) determining a strain value from each of such digital representation and correlating each such strain value with a pressure measurement corresponding to the same point in time to provide a stress-strain relationship.

14. The method of claim 13, further including the step of separately plotting such measured pressure and such digital representations as a function of time to facilitate editing such pressure and digital representations.

15. The method of claim 13, wherein such mechanical characteristics include modulus of elasticity.

16. The method of claim 13, wherein such mechanical characteristics include energy absorption.

17. The method of claim 13, further including the step of making a statistical comparison of such mechanical characteristics with mechanical characteristics obtained from other tests.

18. The method of claim 13, further including the step of constraining such area to a circular area.

* * * * *